United States Patent [19]
Lanza et al.

[11] Patent Number: 5,896,429
[45] Date of Patent: Apr. 20, 1999

[54] METHOD FOR MEASUREMENT OF BLAST FURNACE LINER THICKNESS

[75] Inventors: Richard C. Lanza, Brookline, Mass.; Jeffrey S. Schweitzer, Ridgefield, Conn.

[73] Assignee: Massachusetts Institute of Technology, Cambridge, Mass.

[21] Appl. No.: 08/929,641

[22] Filed: Sep. 15, 1997

[51] Int. Cl.[6] .................................................. G21G 1/12
[52] U.S. Cl. .......................... 376/159; 376/157; 250/358.1; 250/390.06
[58] Field of Search ................................ 376/156–159, 376/249, 258; 250/269.3, 269.6, 358.1, 390.06

[56] References Cited

U.S. PATENT DOCUMENTS

| | | | |
|---|---|---|---|
| 4,785,175 | 11/1988 | Wormald et al. | 376/159 |
| 5,001,342 | 3/1991 | Rambow | 250/269.6 |
| 5,317,605 | 5/1994 | Kosako et al. | 376/159 |
| 5,698,854 | 12/1997 | Gupta | 250/358.1 |

Primary Examiner—Daniel D. Wasil
Attorney, Agent, or Firm—Hamilton, Brook, Smith & Reynolds, P.C.

[57] ABSTRACT

A method and apparatus is disclosed for inspecting a wall to evaluate the remaining thickness of the wall as well as the extent to which the wall has been infiltrated by another material. The disclosure discusses directing photons of radiation and/or neutrons into the wall and measuring and analyzing the radiation emitted from the wall as a result of Compton scattering, pair production, photoelectric absorption and/or neutron absorption. The invention is particularly well suited for inspecting a carbon hearth-wall liner of an iron-smelting blast furnace.

39 Claims, 4 Drawing Sheets

METHOD FOR MEASUREMENT OF BLAST FURNACE LINER THICKNESS

BACKGROUND OF THE INVENTION

In a typical iron production process, a blast furnace is used to reduce iron ore to liquid iron for subsequent processing. A typical blast furnace 10, shown in FIG. 1, can be as high as 100 feet and have a diameter of 50 feet. Inside a steel shell 11 of the furnace 10, three-foot-thick refractory carbon blocks 14 form a hearth-wall liner providing thermal insulation between the molten iron (not shown) and the shell 11.

Figure 1:
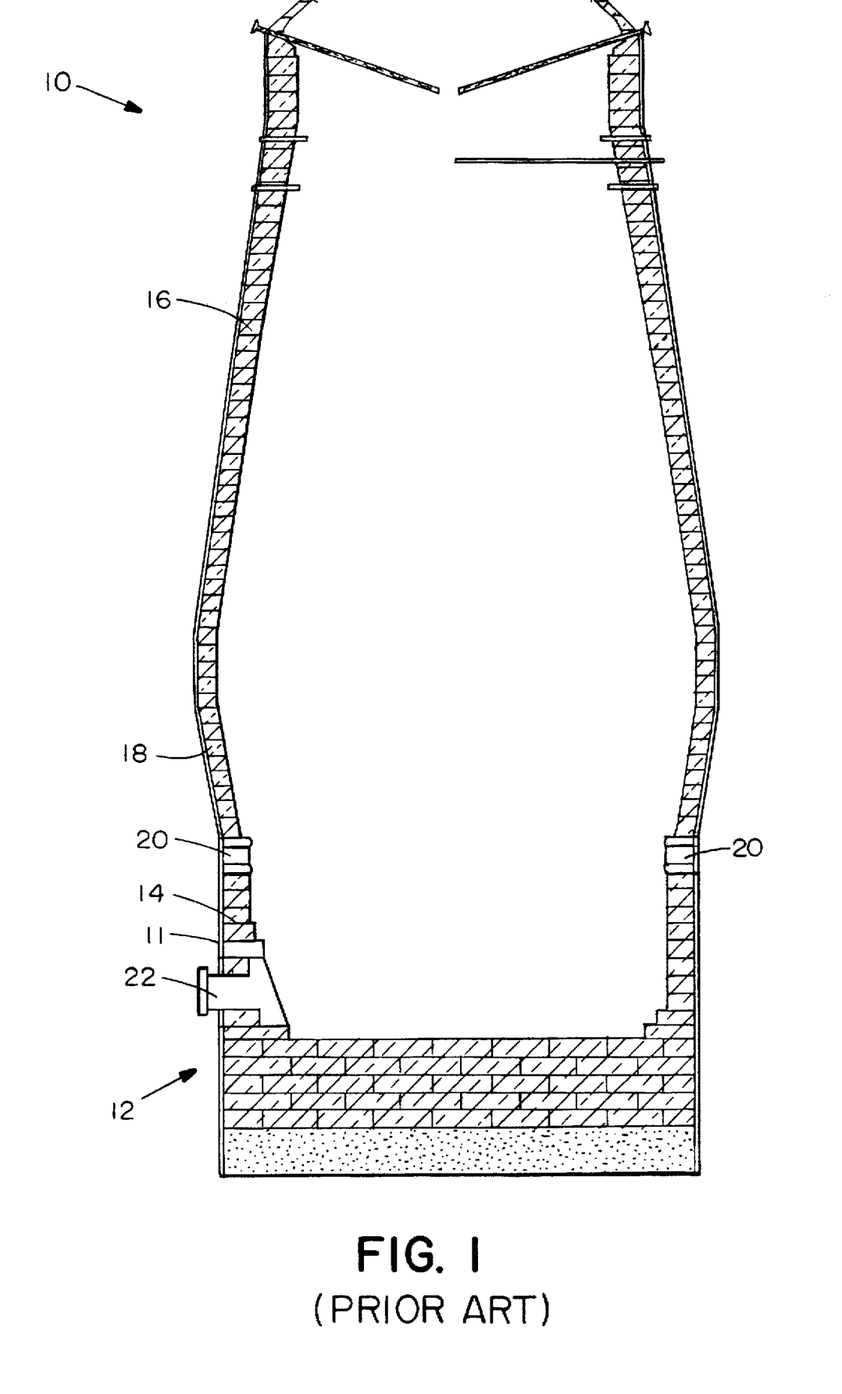
FIG. 1 is a schematic cross-section of a blast furnace.

When the furnace 10 is operating, a burden is fed into the top of the furnace 10. The burden typically includes iron ore, coke and limestone. The iron ore provides iron which serves as the predominant component of steel. The coke combusts to provide the heat required for smelting. Moreover, the coke also supplies needed carbon and carbon dioxide. The limestone serves as a flux to form a fluid slag that can be readily drained from the hearth 12.

As the burden is fed to the furnace 10, it fills the stack 16 as a solid aggregate. The burden is then forced through the stack 16 down into an inverted conical section, known as the bosh 18, where melting starts. A blast of heated air and fuel are introduced through openings 20 at the bottom of the bosh 18, just above the hearth 12 to melt the burden. The resulting iron melt and slag accumulate in the hearth 12 to form a molten bath until drained through a tapping hole 22.

As iron is processed in the furnace 10, the carbon blocks 14 are gradually worn away or weakened due to erosion caused by the mechanical motion of molten iron and also due to infiltration of the molten iron into cracks which develop in the blocks 14. Infiltration and thinning of the carbon blocks 14 has conventionally required that the entire furnace 10 be shut down and relined approximately every six years. For a large furnace, relining requires three to four months downtime of the furnace and consequent loss of production. The cost of relining and shutdown can be $120 million or more.

If relining is delayed, the mechanical integrity of the blocks 14 can fail catastrophically allowing the molten iron to escape through the hearth-wall liner. Furnace failure can easily cost $5 million to $50 million, depending on the extent of damage. In recognition of this danger, blast furnace operators typically err on the conservative side and often replace the hearth-wall lining prematurely. In an effort to better assess the appropriate time to replace the hearth-wall liner, a variety of techniques have been used to evaluate its condition. A common technique uses thermocouples embedded into the hearth-wall liner at various locations. To augment the reliability of these measurements, the use of thermocouples is usually supplemented by periodically drilling through the hearth wall. Although the drilling damages the hearth, it nevertheless enhances the determination of hearth-wall liner thickness. Additionally, invasive optical methods have been developed to evaluate the inner surface of the hearth for wear from inside the furnace when the furnace is shut down and emptied.

SUMMARY

The use of invasive thermocouples and other methods for determining hearth-wall liner thickness often proves inaccurate and difficult to interpret. When thermocouples, for example, are relied upon, thin fissures of iron through the wall may not be detected. In fact, catastrophic furnace failures, in which the molten iron breaks out of the containment, are still reported. The cost of these failures is enormous.

The methods of this invention are based on two techniques for probing with radiation. When used to evaluate the hearth-wall liner of a furnace, the methods of this invention improve the furnace operator's ability to forecast the onset of a failure and, consequently, allow the operator to better assess the appropriate time for hearth-wall liner replacement. The resulting benefits include cost savings, improved planning, decreased downtime, and improved safety. Moreover, the methods are non-invasive and can therefore be performed during normal furnace operation and with greater ease and with less interference than those of the prior art. Further, the methods can be repeated periodically to monitor for changes in the hearth-wall liner.

A method for inspecting a wall in accordance with the invention includes the steps of directing neutrons and photons of radiation into the wall. Radiation is then emitted from the wall as a result of Compton scattering, photoelectric absorption, pair production and neutron absorption. This radiation is measured and analyzed to evaluate the remaining thickness of the wall and the extent to which the wall has been infiltrated by another material. Alternatively, either the step of directing radiation into the wall or the step of directing neutrons into the wall can be used in the absence of the other.

In a preferred embodiment, the radiation directed into the wall is in the form of gamma rays and the inspected wall includes a hearth-wall liner comprising carbon. The hearth-wall liner is adapted to contain a molten metal, such as iron, in a furnace, and the inspection is performed from a position outside the furnace. In this embodiment, the material for which infiltration into the wall is evaluated is the molten metal contained by the hearth-wall liner.

When neutrons are directed into the wall, the neutrons scatter until absorbed, at which point, signature gamma rays are produced. The rate at which neutrons are absorbed is a function of the neutron-absorption cross section of the medium in which the neutrons travel. In short, the neutrons will be absorbed more quickly in a medium of larger cross section. In accordance with one aspect of the invention, the analysis includes evaluating, as a function of time, measurements of emitted gamma rays produced by neutron absorption to determine the amount of iron infiltration into the carbon hearth-wall liner.

The analysis of radiation emitted from the wall as a result of directing radiation into the wall is more complex than that for neutrons. However, the methods of this invention also encompass techniques for evaluating the measurements of radiation emitted from the wall as a result of the incident radiation. For example, when a gamma ray/nucleus interaction leads to pair production, gamma rays having an energy of 511 keV are produced. In one embodiment, the rate of pair production, which reflects the composition of the matter through which the gamma rays travel and is therefore sensitive to the overall thickness of a hearth-wall liner, is determined by monitoring for the effects of 511 keV gamma rays produced within the hearth wall and molten iron.

Further, the emitted radiation can be plotted as a function of the energy of the emitted photons. The peak of this plot typically falls in the range of about 200 keV to about 300 keV. The magnitude of this peak, in particular, as well as the magnitude of other parts of the spectrum, is dependent upon the thickness of different compositions penetrated by the gamma rays. Another embodiment utilizes this dependance to determine the thickness of a hearth-wall liner by analyzing the magnitude of the different portions of the spectrum, particularly the range between 200 and 511 keV, for a given set of measurements.

A third embodiment uses the ratio of the number of photons emitted from the wall to the number of photons directed into the wall to determine the thickness of the hearth-wall liner because this ratio, as well, is dependent upon the composition of penetrated matter. Further, these measurements are preferably performed by a plurality of detectors and the measurements recorded by each detector can then be compared to determine the extent to which the gamma rays have scattered and, as a result, determine the thickness of the hearth-wall liner.

In accordance with another aspect of this invention, a computer Monte Carlo simulation program, such as MCNP or COG, is used to simulate the behavior of photons in media of specified composition and of varying thicknesses. Use of a suitable Monte Carlo program is described in MCNP™—A GENERAL MONTE CARLO N- PARTICLE TRANSPORT CODE (Judith F. Briesmeister, ed., Version 4A, 1993), incorporated herein in its entirety by reference. The program is then used to produce a simulated readout of radiation detected outside the furnace. When the photons are actually directed into a wall in accordance with the methods of this invention, the radiation measurements are then compared to the simulated results to determine the thickness of the hearth-wall liner.

In a preferred embodiment of an apparatus used to perform the methods of this invention, an electron accelerator is used to direct bremsstrahlung radiation having an energy at least as great as the pair production threshold of 1.022 MeV, and preferably 3 to 8 MeV, into the hearth-wall liner. Further, the electron accelerator can also be used to trigger the emission of neutrons directed into the wall by, for example, placing a beryllium target in the path of the stream of photons emitted by the electron accelerator. Alternatively, a pulsed sealed neutron source can be used to provide the neutrons that are directed into the wall.

DESCRIPTION OF PREFERRED EMBODIMENTS

A. Introduction

A pair of methods is used to safely and reliably evaluate the thickness and integrity of the liners of the hearth of a blast furnace. The first method involves the transport of gamma rays (specifically, bremsstrahlung radiation) directed into the hearth-wall liner. The second involves the die away of thermal neutrons directed into the hearth-wall liner. Either method can be used independently to evaluate the condition of a hearth-wall liner. However, the two methods are used to greatest advantage when they are used together because of the complementary information that each provides.

The term, "gamma rays," may be used interchangeably herein with "photons" and "electromagnetic radiation." However, the term, "gamma rays," most correctly refers to radiation produced by nuclear processes.

Figure 2:
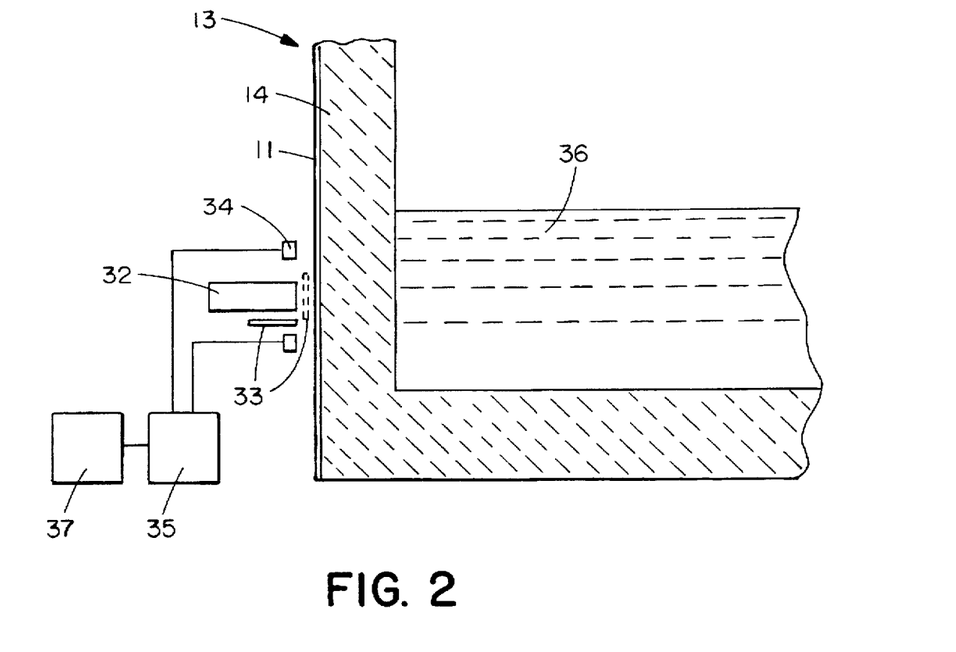
FIG. 2 is a schematic cross-sectional illustration of a portion of a blast furnace 10 and a first embodiment of an apparatus for directing gamma rays and neutrons into the sidewall of the blast furnace 10 and for detecting the radiation emitted from the sidewall.

An embodiment of the apparatus for performing the disclosed methods is illustrated in FIG. 2. The radiation source 32 is a small compact 6 MeV electron linear accelerator (LINAC) directed toward the wall 13 opposite the molten iron 36. The hearth-wall liner 14 typically comprises carbon and is surrounded along its exterior by a one-to-two-inch-thick steel shell 11. The radiation source 32 is one meter long with a weight of approximately 40 kg and is designed for field use. It produces gamma rays of up to 6 MeV in energy. Moreover, a beryllium target 33 may be moved into the path of the gamma rays, as shown by the broken-line image, to produce neutrons for the decay-time measurements. Alternatively, the radiation source 32 may be supplemented or replaced by a small sealed pulsed neutron generator. The source 32 is surrounded by gamma-ray detectors 34 positioned to detect gamma radiation emitted from the wall 13 as a result of the gamma rays and neutrons directed into the wall 13. Any suitable gamma-ray detector may be used. For example, the detectors may be semiconductor detectors, such as germanium or cadmium zinc telluride. Alternatively, the detectors may be scintillators, such as sodium iodide (thallium-doped), barium fluoride, bismuth germanate, one of the rare earth oxyorthosilicates (cerium-doped) or a rare earth aluminate (cerium-doped) porovskite, for example, with an associated photosensitive device such as a photomultiplier tube (PMT) or avalanche photo diode (APD). As another alternative, the detectors may be gas detectors, such as high pressure xenon. The radiation/neutron source 32 and its associated detectors 34 are portable and may be moved vertically up the wall 13 of the furnace as well as horizontally to traverse the entire area to be scanned.

The cylindrical side wall of the crucible-shaped hearth 12 of a blast furnace 10, illustrated in FIG. 1, is particularly well suited for evaluation by these methods.

B. Gamma-Ray Transport

In the first of the two methods for evaluating the hearth-wall liner, high-energy bremsstrahlung radiation 38 is directed at the hearth sidewall 13 from outside the furnace 10, and the radiation emitted back out of the wall 13 is measured and analyzed. As noted previously, the bremsstrahlung radiation is produced by a LINAC and comprises gamma ray photons of at least 1.02 MeV, and, preferably, between about 3 and 8 MeV, emitted by accelerated electrons after colliding with the nuclei of atoms in a target within the LINAC. The gamma rays penetrate the hearth 12, allowing testing to be performed without draining the furnace, without placing probes in the furnace, without breaching the integrity of the outer steel shell 11 and without suspending equipment down into the furnace from above. Using gamma rays as described herein, the test can be performed without any disruption of furnace operation.

Figure 3:
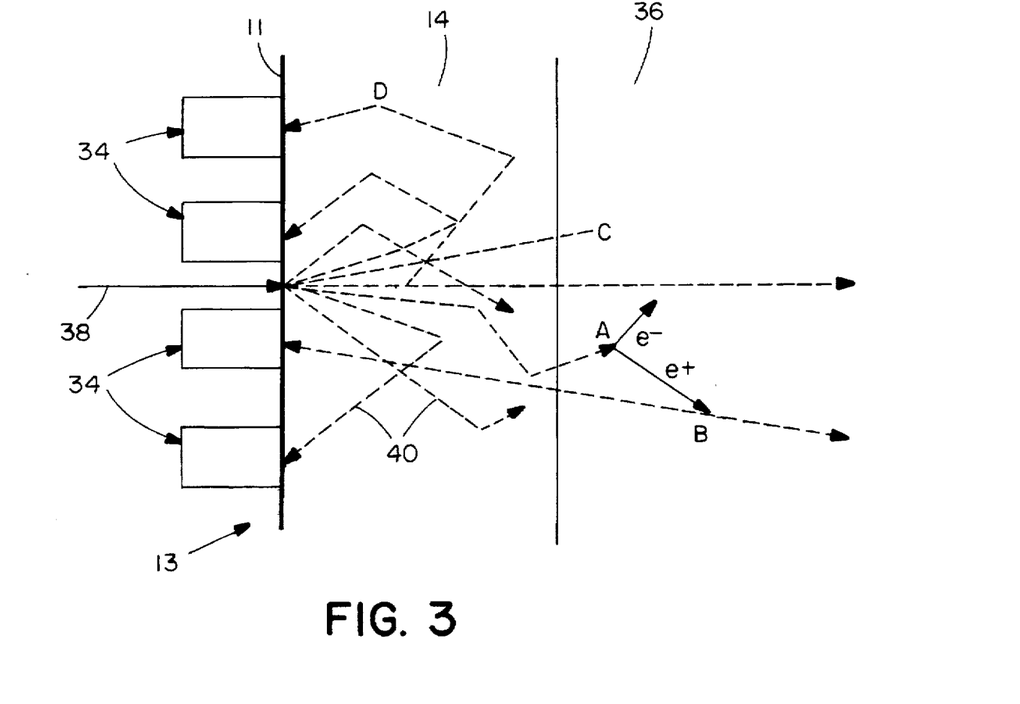
FIG. 3 is a representative illustration of the paths of gamma rays directed into the sidewall of a blast furnace.

As the photons collide with the atoms that comprise the hearth-wall liner 14, and, perhaps also, the iron bath 36, as shown in FIG. 3, each photon 40 may interact with an atom to produce at least one of the following three results: pair production, Compton scattering or photoelectric absorption.

First, if the energy of the photon is above 1.02 MeV, the photon may be completely absorbed by the nucleus resulting in pair production. Pair production occurs when the energy of the photon is converted into an electron and a positron, each with a rest-mass energy of 511 keV and a kinetic energy that depends on the energy of the incident gamma ray. A positron is a particle with the mass of an electron but with a positive charge. As the positron and electron move away from their point of origin, each loses energy by ionization. When the positron energy drops low enough, the positron combines with an electron, and both are annihilated to produce a pair of 511 keV photons radiated in opposite directions. Pair production is illustrated by the photon-interaction representation, A, in FIG. 3. Annihilation is illustrated by the representation, B, along the same path.

The probability of pair production is directly proportional to the square of the atomic number of the medium. Though the exact energy dependence of pair production is complex, a reasonable approximation of the probability of pair production per unit track length, $\Sigma_{pair}$, at higher energies is given by:

$$\Sigma_{pair} = K_{pair} \rho_{nuc} Z^2 \ln E_\gamma,$$

where $K_{pair}$ is a constant, $\rho_{nuc}$ is the nuclear density, Z is the atomic number and $E_\gamma$ is the energy of the incident photon.

Second, the photon may collide with an electron and transfer all of its energy to the electron in the form of kinetic energy. In such a case, the electron is ejected from its atom, and the photon disappears in what is known as the photoelectric effect. An example of the photoelectric effect is designated by the photon path representation, C, in FIG. 3. The ejection of the electron leaves a vacancy in one of the atom's orbitals which will typically be filled by an electron in an outer orbital of higher energy level. As the outer electron changes orbitals to fill the vacancy, energy is released in a photon which can be easily recognized because its energy will be that of the difference in energy between the respective orbitals of the atom. The ejected electron has an energy which is the difference between the energy of the incident gamma ray and the binding energy of the electron in its atomic shell. Like pair production, photoelectric absorption increases with increasing atomic number. The absorption probability, $\Sigma_a$, per track length of photons is approximately given by:

$$\Sigma_a = K_a Z^{3.6} \Sigma_e / E_\gamma^{3.15},$$

where $\rho_e$ is the electron density.

Third, the photon may collide with an electron and transfer some of its energy to the electron, ejecting the electron from its orbit. Meanwhile, the photon deflects and continues through the medium, albeit at a lower energy. This process occurs mainly with electrons in the outer orbital of an atom and is known as Compton scattering. Compton scattering dominates at energies above those where photoelectric absorption is dominant yet below those where pair production becomes important. Compton scattering is illustrated by the photon-interaction representation, D, in FIG. 3. The difference between Compton scattering and photoelectric absorption is that the photon loses only part of its energy when it undergoes Compton scattering. The likelihood of scatter per unit track length, $\Sigma_s$, is a function only of electron density and photon energy and is given by:

$$\Sigma_s = K_s \rho_e / E_\gamma$$

The energy of the photon after it is scattered is inversely related to the angle by which it is scattered. After the photon scatters, the reduced-energy photon will likely interact with another atom in one of the three ways discussed.

Because carbon, of which the hearth-wall liner 13 of the hearth 12 is comprised, has a relatively low atomic number, 6, pair production and photoelectric absorption rarely occur in carbon. Instead, a photon traveling through carbon is much more likely to undergo Compton scattering. In contrast, the iron of the bath has a much higher atomic number, 26. As a result, the probability of pair production in iron is at least a factor of ten larger than in carbon, especially where the photon energy is greater than 3–4 MeV. Thus, we expect pair production at the surface of the iron and subsequent production of photons with the energy characteristic of this process, 511 keV.

The equations, provided above, are utilized to establish a strategy for distinguishing carbon from iron. In a thick piece of carbon, the dominant form of photon interaction will be Compton scattering, whereas in iron, pair production will be much larger. These differences are even more pronounced when one accounts for the difference in density between iron and carbon in establishing absolute rates. Accordingly, the radiation emitted from the wall will vary according to the thickness of carbon that the photon must pass through before reaching the iron. The signature of the photons detected at or near the surface of the wall can then be matched to radiation patterns characteristic of walls having hearth-wall liners of varying thicknesses to closely estimate the actual thickness of the hearth-wall liner measured. The gamma-ray source and detectors are then moved to different locations on the sidewall for repeated measurements to better evaluate the entirety of the sidewall.

The exact details of the multiple scatter and its dependence on carbon thickness can best be predicted using simulation, as for example by the MONTE CARLO N-PARTICLE CODE™ (MCNP). MCNP is designed to simulate the transport of neutrons, photons and/or electrons through a medium or plurality of media. When a user enters the appropriate description (geometry and materials) of the media and the source, the code sequentially simulates each of the individual probabilistic events that comprise the transport of the particle through the medium. When simulating the interaction or sequence of interactions between a photon and the medium, the code is used to statistically sample a probability distribution of each of the possible forms of photon/atomic interaction, described above, using a random number generator. As the simulated particle proceeds from a source through each simulated interaction, the code is used to track the decrease in energy and the change in direction that each interaction produces until the eventual death of the particle in some terminal category, such as absorption, pair production, or escape. As the histories of more simulated particles are collected, the release of the various types of detectable radiation is tallied to produce a model estimating actual behavior in a system having the specified characteristics.

By modifying the characteristics of a carbon hearth-wall liner that are input to the MCNP—particularly, the thickness of the carbon—a range of results can be obtained. Since the area tested will normally be surrounded by a steel shell, the simulation should be configured to include the characteristics of this shell so that its influence can be accounted for. After confirming the accuracy of these results by comparing the MCNP values with actual test data, the MCNP values can be matched to field measurements to provide a reliable estimate of carbon thickness. Alternatively, algorithms can be empirically developed that relate changes in the spectral response to changes in the carbon thickness.

Figure 4:
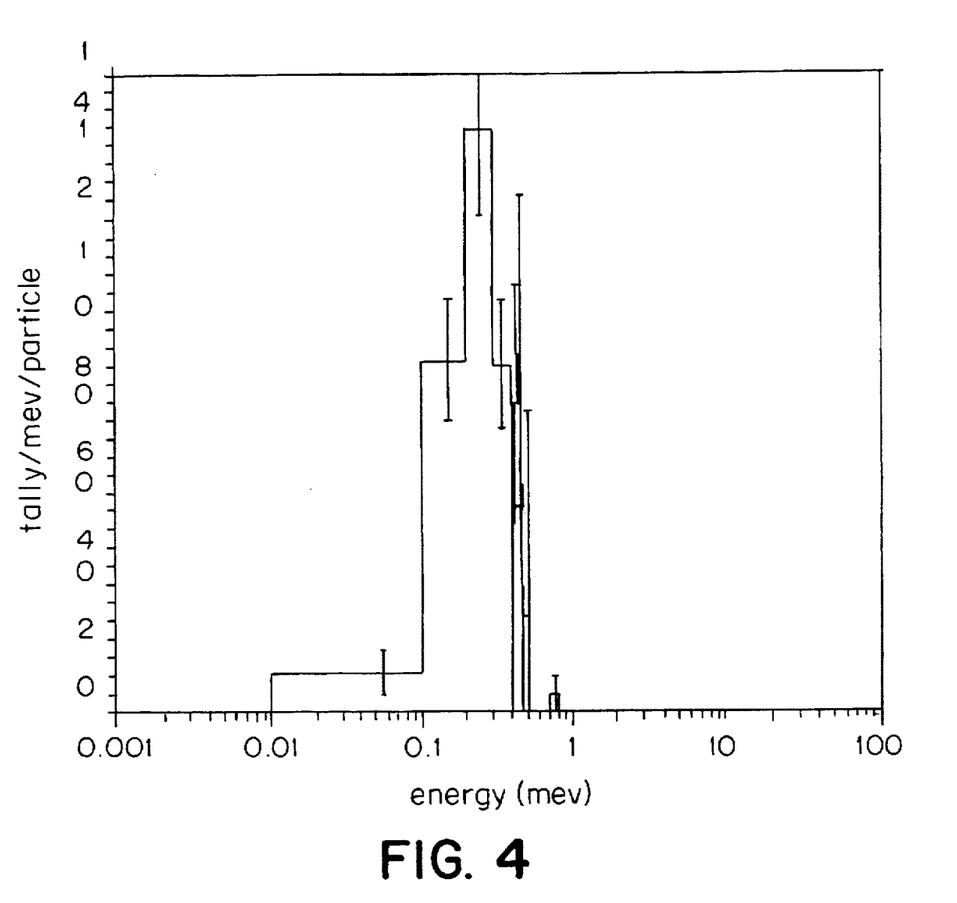
FIG. 4 is a chart of the measured energy spectrum of gamma rays detected in a simulation of gamma rays directed into a wall including a 5 cm-thick steel shell and a 90 cm-thick carbon hearth-wall lining enclosing molten iron.
Figure 5:
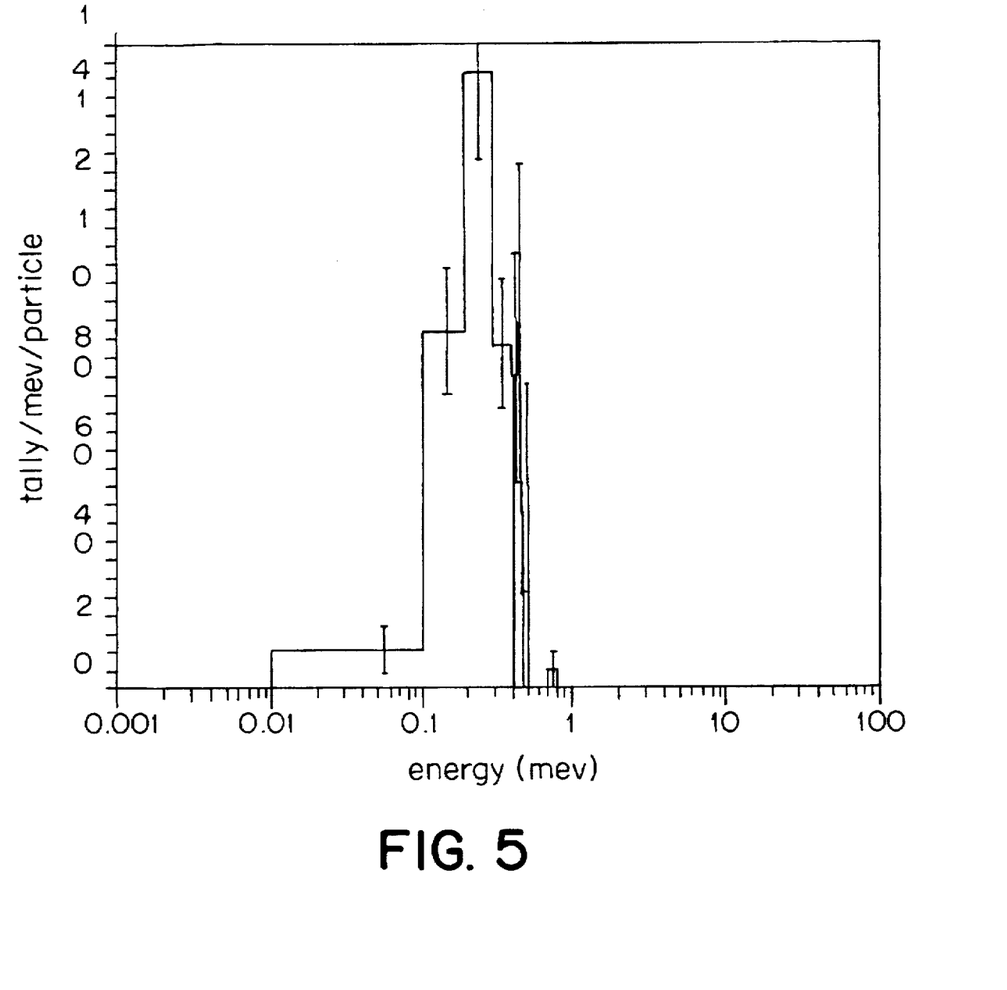
FIG. 5 is a chart of the measured energy spectrum of gamma rays detected in a simulation of gamma rays directed into a wall including a 5 cm-thick steel shell and a 100 cm-thick carbon hearth-wall lining enclosing molten iron.

Using MCNP, simulations of gamma ray transport through a hearth wall with a 5-cm-thick steel shell and a carbon liner having a thickness of either 90 or 100 cm were conducted. The simulated energy spectra produced at a point 20 cm from the point on the wall where radiation is incident are shown in FIGS. 4 and 5. The peak of the simulated energy spectrum, between 200 and 300 keV is approximately 5% greater in the simulation for the 100-cm-thick carbon hearth-wall liner, shown in FIG. 5, than the peak for the 90-cm-thick carbon hearth-wall liner. These results validate the premise that the methods of this invention can be used to differentiate between hearth-wall liners of different thicknesses.

As an alternative to MCNP, a similar simulation program, known as COG™, developed at Lawrence Livermore National Laboratory may be used, as may other Monte Carlo programs.

C. Neutron Decay Time

A second procedure for inspecting the carbon hearth-wall liner of a blast furnace involves directing neutrons into the hearth-wall liner and measuring the time between emission and absorption of the neutron. The neutron scatters through the medium of the wall, and sometimes through the molten iron, losing energy until it reaches thermal energies. At thermal energies, the neutron diffuses through the medium until captured by a nucleus, thereby producing a gamma ray that can the furnace outside the furnace.

The basis for this approach is the fixed rate at which thermal neutrons will be absorbed in a given medium. The rate at which the neutrons are absorbed depends on the macroscopic thermal-neutron-absorption cross section, $\Sigma$, of the medium. The macroscopic thermal-neutron-absorption cross section is the average microscopic thermal-neutron-absorption cross section per unit volume of the medium. The rate at which thermal neutrons are absorbed in a medium is given by:

$$dN/dt = N_0 e^{-\Sigma vt},$$

where $N_0$ is the number of neutrons at time $t=0$ and $v$ is the velocity of the neutrons.

The major advantage of using this technique in this particular context is that the neutron absorption cross sections for carbon and iron are dramatically different. The microscopic thermal neutron absorption cross section for iron is 2.56 barns ($10^{-24}$ cm$^2$), while that for carbon is 3.4 millibarns. Thus, the sensitivity of a measurement of the thermal neutron decay time for iron in a predominantly carbon environment is about a factor of a thousand. As a result, the detection of a 5 percent change in the thermal decay time should allow the operator to detect an infiltration of iron into carbon at about 50 parts per million.

The measurement is performed by producing a short burst of high-energy neutrons. The burst in this situation should be about one millisecond in duration, though narrower burst widths are quite acceptable. The high-energy neutrons can be provided using the same compact electron accelerator used to produce the bremsstrahlung radiation for the gamma-ray transport measurement. The neutrons are supplied by placing a beryllium secondary target in the path of the gamma rays. Alternatively, the neutrons can be supplied by a small sealed neutron generator, such as those used in the oil well logging industry.

The high-energy neutrons scatter in the furnace material, gradually losing energy until they approach thermal energies. While at thermal energies, the neutrons diffuse through the furnace material until they are captured by nuclei. Each capture event is accompanied by the essentially instantaneous production of one or more gamma rays that are detected by a gamma-ray detector outside the furnace, where the gamma-ray detector is of a type mentioned previously. The detection of gamma rays is recorded as a function of time relative to the end of the burst of neutrons. Following a sufficient interim, additional neutron bursts are provided to produce more gamma rays, which are detected and recorded to build the necessary level of statistical accuracy for the lifetime determination. The number of gamma rays detected as a function of time is fit by an appropriate mathematical function to determine the decay time of neutrons directed into the wall. Moreover, the neutron source and detectors are moved to different locations on the sidewall, where the measurements are repeated and a better evaluation of the entirety of the sidewall is obtained.

The recorded measurements are then fed to a personal computer 35 to determine the amount of infiltrated iron by correlating the neutron decay times (or the time dependence of the gamma-ray spectrum) with known iron infiltration parameters. The proper correlation can be established through mathematical analysis, actual testing, and/or Monte Carlo simulation, using codes such as MCNP. Once the computer 35 has performed this correlation, a value for the estimated thickness of the hearth-wall liner is transmitted to a display 37.

Neutron decay measurements have been used to probe earth formation properties behind steel casings. However, they have not been applied in an industrial application, as considered here. The expected depth sensitivity in this environment is expected to be about 70–90 cm which is sufficiently deep to monitor the region from the outer surface of the furnace to a depth near the iron-carbon interface.

D. Equivalents

While this invention has been particularly shown and described with references to preferred embodiments thereof, it will be understood by those skilled in the art that various changes in form and details may be made therein without departing from the scope of the invention as defined by the appended claims. For example, and without limitation, infiltration of other molten metals, besides iron may be analyzed in a similar fashion utilizing the apparatus and methods described herein.

The invention claimed is:

1. A method for inspecting a carbon hearth-wall liner inside a metal jacket of a furnace from outside the furnace, the carbon hearth-wall liner adapted to contain molten metal, comprising the following steps:
   directing photons of radiation into the hearth-wall liner;
   directing neutrons into the hearth-wall liner;
   measuring radiation emitted from the hearth-wall liner as a result of having directed the photons and the neutrons into the hearth-wall liner; and
   analyzing the measurements to determine the remaining thickness of the hearth-wall liner and the extent to which the molten metal has infiltrated the hearth-wall liner.

2. The method of claim 1, wherein the photons directed into the hearth-wall liner have an energy greater than a pair production threshold of 1.02 MeV.

3. The method of claim 2, wherein the radiation is emitted in photons and the analysis of the measurements further includes evaluating the number of photons emitted with an energy of approximately 511 keV.

4. The method of claim 2, wherein the radiation is emitted in photons and the analysis of the measurements further includes evaluating the number of photons emitted with an energy in a range between about 200 keV and about 511 keV.

5. The method of claim 2, wherein the radiation emitted from the hearth-wall liner is detected by a plurality of detectors and the determination of the remaining thickness of the hearth-wall liner further includes comparing the amount of radiation measured in each of the detectors.

6. The method of claim 2, wherein an electron accelerator triggers the emission of neutrons directed into the hearth-wall liner.

9

7. The method of claim 2, wherein the analysis of the measurements includes comparing the measurements with values predicted using a simulation program.

8. The method of claim 7, wherein the photons directed into the hearth-wall liner include bremsstrahlung radiation produced by an electron accelerator.

9. The method of claim 8, wherein the bremsstrahlung radiation has an energy of 3 to 8 MeV.

10. The method of claim 1, wherein the analysis of the measurements includes evaluating, as a function of time, emission of radiation produced by neutron absorption.

11. The method of claim 1, wherein the analysis of the measurements includes comparing the measurements with values predicted using a simulation program.

12. The method of claim 1, wherein the molten metal is iron.

13. A method for inspecting a carbon hearth-wall liner of a furnace from outside the furnace, the carbon hearth-wall liner containing molten metal, comprising the following steps:

directing photons of gamma radiation into the hearth-wall liner;

using at least one radiation detector to measure radiation backscattered out of the hearth-wall liner and to measure gamma radiation produced as a result of pair production by the gamma radiation directed into the hearth-wall liner; and comparing the amount of backscattered radiation to the amount of radiation directed into the hearth-wall liner to estimate the thickness of the hearth-wall liner.

14. The method of claim 13, wherein the gamma radiation directed into the hearth-wall liner has an energy greater than the pair production threshold of 1.02 MeV.

15. The method of claim 14, wherein the radiation emitted from the hearth-wall liner is detected by a plurality of detectors and the determination of the remaining thickness of the hearth-wall liner further includes comparing the amount of radiation measured in each of the detectors.

16. The method of claim 14, further including the step of comparing the measurements from the radiation detector to values predicted using a simulation program.

17. The method of claim 16, wherein the photons directed into the hearth-wall liner include bremsstrahlung radiation having an energy of 3 to 8 MeV.

18. The method of claim 13, wherein the metal is iron.

19. A method for inspecting a carbon hearth-wall liner of a furnace from outside the furnace, the carbon hearth-wall liner adapted to contain molten metal, comprising the following steps:

directing neutrons into the hearth-wall liner;

using a radiation detector to monitor for gamma radiation produced when the neutrons are absorbed;

measuring the time elapsed between the neutrons being directed into the hearth-wall liner and the production of the gamma radiation; and using the measurements of elapsed time to estimate the amount of metal in the volume of the hearth-wall liner.

20. The method of claim 19, wherein the radiation emitted from the hearth-wall liner is detected by a plurality of detectors and the determination of the remaining thickness of the hearth-wall liner further includes comparing the amount of radiation measured in each of the detectors.

21. The method of claim 19, further including the step of comparing the measurements from the radiation detector to values predicted using a simulation program.

22. The method of claim 19, wherein the metal is iron.

10

23. A method for inspecting a wall comprising the following steps:

directing electromagnetic radiation into the wall;

directing neutrons into the wall; and measuring and analyzing radiation emitted from the wall as a result of having directed the electromagnetic radiation and the neutrons into the wall to evaluate the remaining thickness of the wall and to determine the extent to which the wall has been infiltrated by another material.

24. The method of claim 23, wherein the electromagnetic radiation directed into the wall has an energy greater than a pair production threshold of 1.02 MeV.

25. The method of claim 24, wherein the radiation is emitted in gamma-ray photons and the analysis of the emitted-radiation measurements further includes evaluating the number of photons emitted having an energy of approximately 511 keV.

26. The method of claim 24, wherein the radiation is emitted in photons and the analysis of the measurements further includes evaluating the number of photons emitted with an energy in a range between about 200 keV and about 511 keV.

27. The method of claim 24, wherein the radiation emitted from the wall is detected by a plurality of detectors and the determination of the remaining thickness of the wall further includes comparing the amount of radiation measured in each of the detectors.

28. The method of claim 24, wherein an electron accelerator triggers the emission of neutrons directed into the wall.

29. The method of claim 24, wherein the analysis of the emitted-radiation measurements includes comparing the emitted-radiation measurements with values predicted using a simulation program.

30. The method of claim 29, wherein the photons directed into the wall include bremsstrahlung radiation produced by an electron accelerator.

31. The method of claim 30, wherein the bremsstrahlung radiation has an energy of 3 to 8 MeV.

32. The method of claim 23, wherein the analysis of the emitted-radiation measurements includes evaluating, as a function of time, emission of gamma rays produced by neutron absorption.

33. The method of claim 32, wherein the analysis of the emitted-radiation measurements includes comparing the emitted-radiation measurements with values predicted using a simulation program.

34. An apparatus for inspecting a carbon hearth-wall liner inside a metal jacket of a furnace from outside the furnace, the carbon hearth-wall liner adapted to contain molten metal, comprising:

a photon generator for generating photons of gamma radiation that are directed into the hearth-wall liner;

a neutron generator for directing neutrons into the hearth-wall liner;

at least one detector for detecting and measuring photons of radiation emitted from the hearth-wall liner as a result of having directed the radiation and the neutrons into the hearth-wall liner; and a computer for analyzing the measurements to determine the remaining thickness of the hearth-wall liner and the extent to which the molten metal has infiltrated the hearth-wall liner.

35. The apparatus of claim 34, wherein the radiation emitted from the hearth-wall liner is detected by a plurality of detectors.

36. The apparatus of claim 34, wherein the neutron generator comprises the photon generator and a neutron-emitting target.

37. The apparatus of claim 36, wherein the neutron-emitting target includes beryllium.

38. The apparatus of claim 34, wherein the photon generator is a linear accelerator capable of producing bremsstrahlung radiation.

39. The apparatus of claim 38, wherein the bremsstrahlung radiation has an energy of about 3 to about 8 MeV.

* * * * *